United States Patent [19]

Lauritzen

[11] Patent Number: 4,607,633
[45] Date of Patent: Aug. 26, 1986

[54] UNITARY ADHESIVE BANDAGE AND PACKAGE

[75] Inventor: Nels J. Lauritzen, Piscataway, N.J.

[73] Assignee: Johnson & Johnson Products, Inc., New Brunswick, N.J.

[21] Appl. No.: 743,260

[22] Filed: Jun. 10, 1985

Related U.S. Application Data

[62] Division of Ser. No. 479,599, Mar. 28, 1983, Pat. No. 4,545,372.

[51] Int. Cl.⁴ .............................................. A61L 15/00
[52] U.S. Cl. ................................................... 128/156
[58] Field of Search ........................ 128/156; 428/221

[56] References Cited

U.S. PATENT DOCUMENTS 4,360,015 11/1982 Mayer ................................ 128/156
4,530,353 7/1985 Lauritzen ........................... 128/156

Primary Examiner—Gregory E. McNeill
Attorney, Agent, or Firm—Wayne R. Eberhardt

[57] ABSTRACT

An adhesive bandage and integral wrapper therefor is constructed of a continuous length of bulky, nonwoven bandage and wrapper material which is preferably a nonwoven fabric batt constructed at least in part of heat-fusible fibers. The bandage pad is formed by a Z-fold in the bandage portion of the material. The adhesive wing portions of the bandage are compacted and fused prior to the application of a pressure-sensitive adhesive. The wrapper portion of the product may be entirely nonwoven fabric compacted and heat-fused and coated with an adhesive release surface, or may be formed in part of polyethylene or similar film. The wrapper material is folded around the bandage and sealed on three edges to totally enclose the bandage.

14 Claims, 12 Drawing Figures

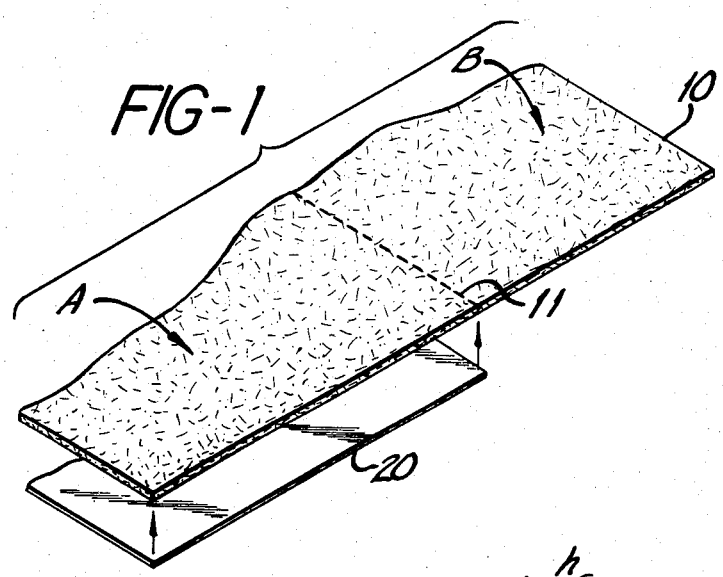
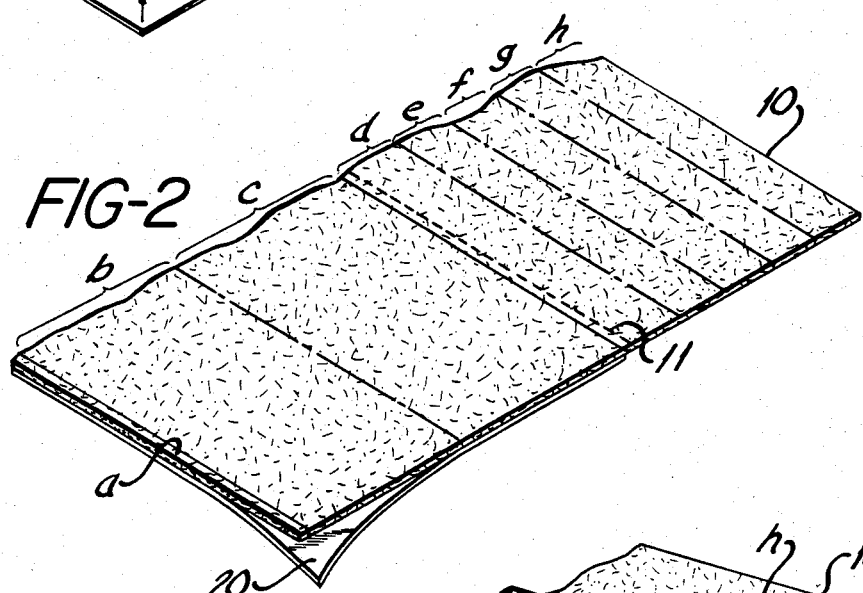
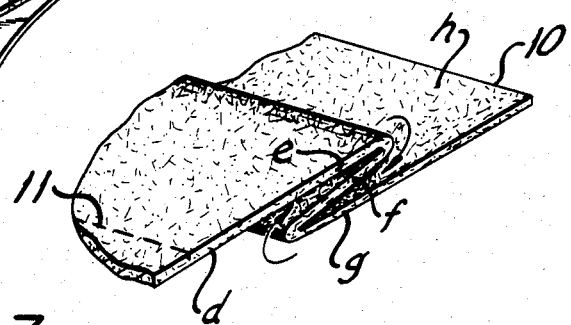

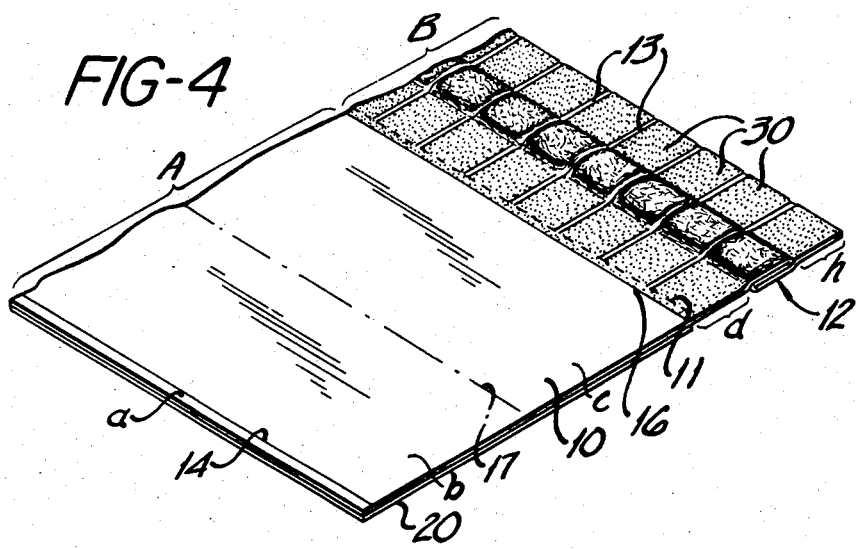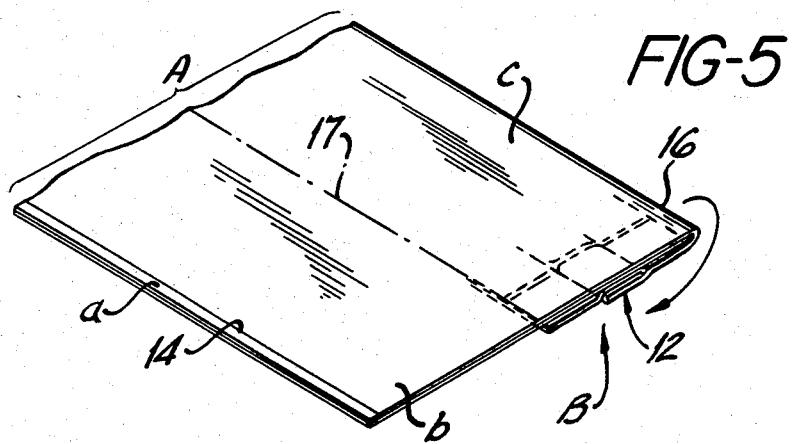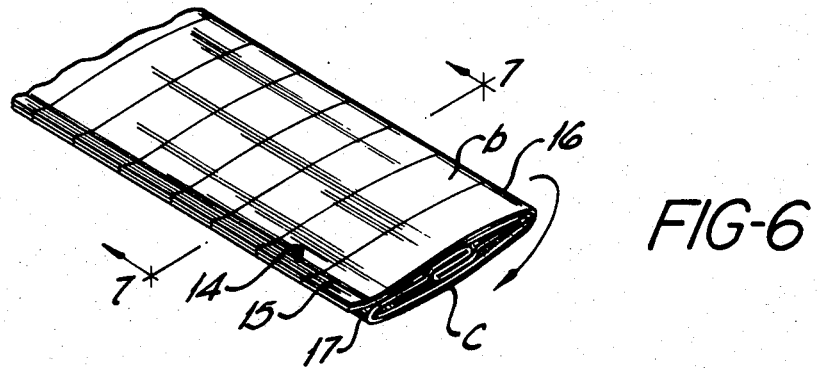

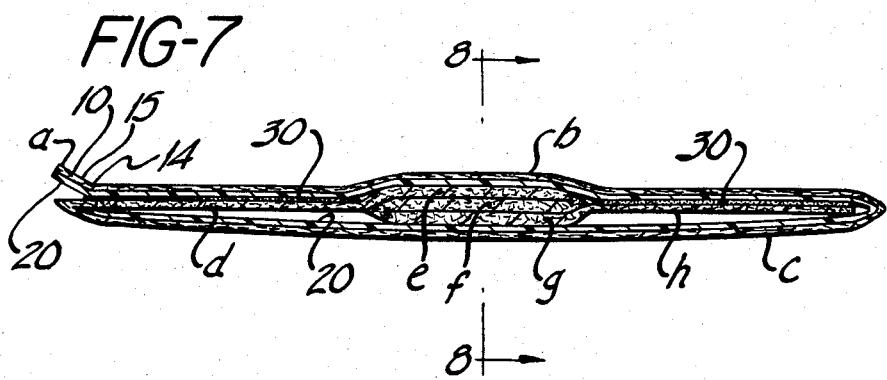
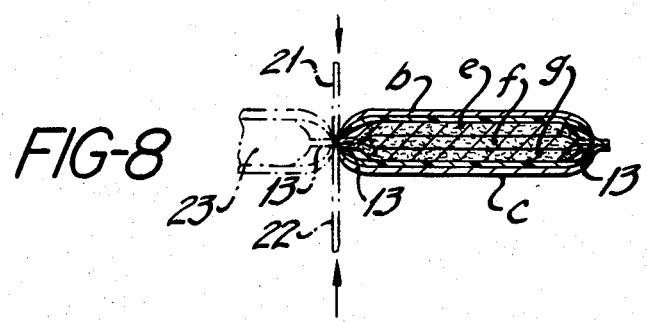
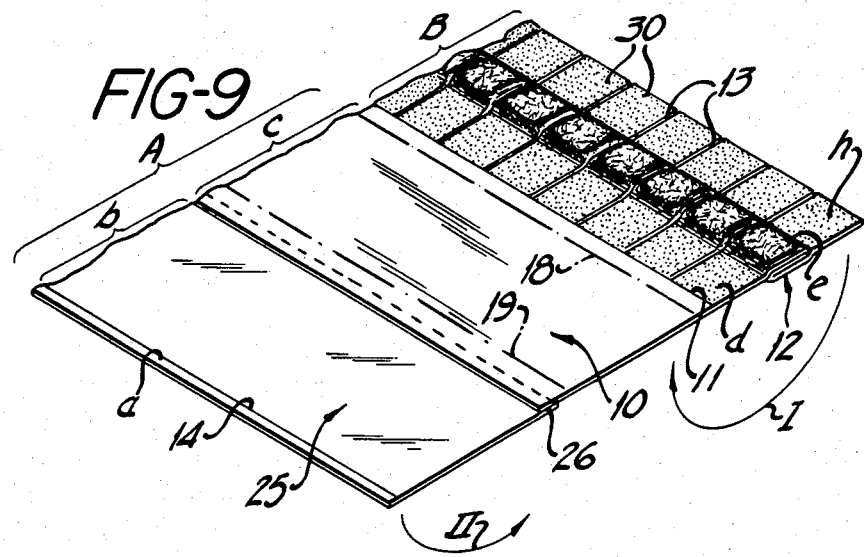

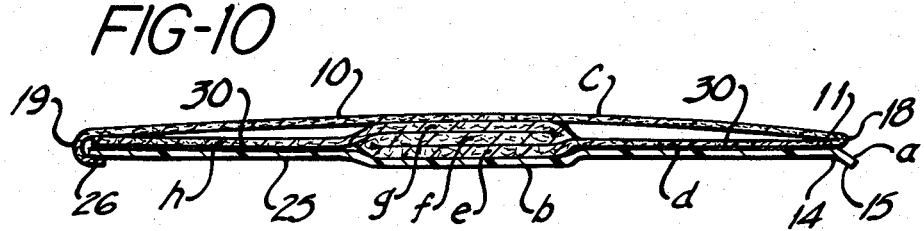
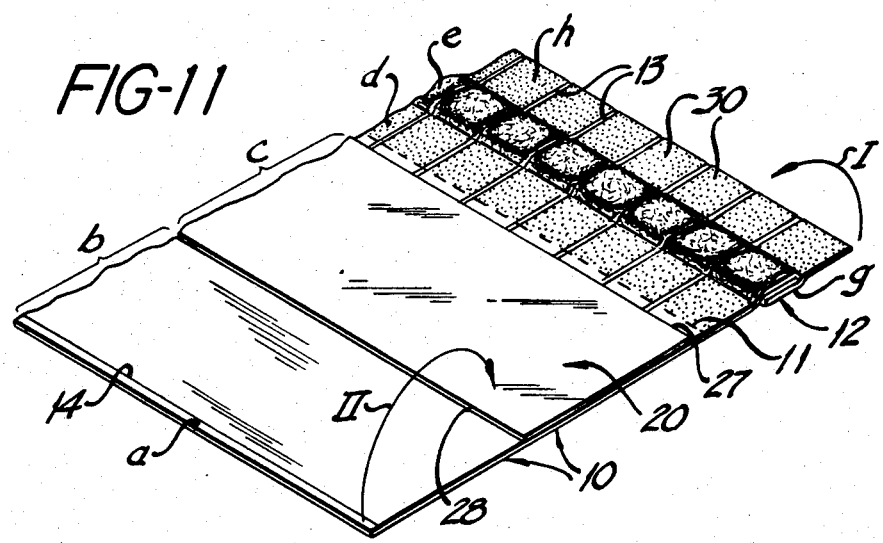
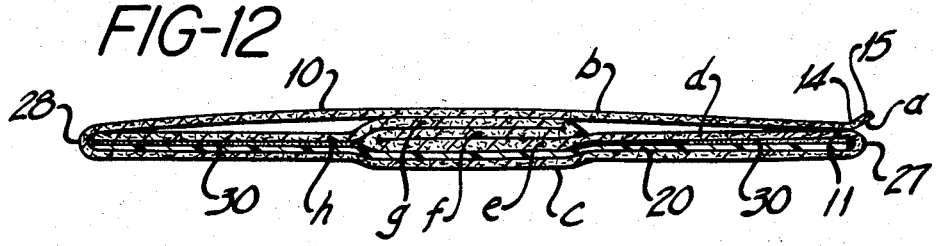

UNITARY ADHESIVE BANDAGE AND PACKAGE

This application is a divisional of Ser. No. 479,599, filed on Mar. 28, 1983, now U.S. Pat. No. 4,545,372.

FIELD OF INVENTION

The present invention relates to adhesive bandages comprising a central pad area and adjacent adhesive areas, and more particularly, to an adhesive bandage and package therefor constructed as a unit from a continuous length of a bulky, nonwoven fabric.

BACKGROUND OF THE INVENTION

Adhesive bandages comprising a central pad area and adjacent adhesive areas are well-known in the art and popular as first aid wound dressings. Current bandages generally comprise an elongated strip of cloth or plastic backing material coated on one surface with a pressure sensitive adhesive. A gauze or sponge pad is secured to the adhesive surface in a central location to serve as the wound cover. The wound facing surface of the pad may be plastic-coated or otherwise treated to prevent the pad from adhering to the wound. Plastic-coated release strips are placed over the adhesive areas and the entire assembly is enclosed in a sealed package and sterilized to be ready for use.

The adhesive bandages of the prior art are characterized by their construction of two basic components—the adhesive coated backing material and the wound covering pad material. While such bandages are effective and desirable products, the assembly of the component materials during production results in increased manufacturing and inventory costs. In addition, the packaging of individual bandages requires additional handling and materials which further increases manufacturing costs.

It is accordingly an object of the present invention to provide an improved adhesive bandage. It is a further object of this invention to provide a low cost adhesive bandage through the use of inexpensive materials and low cost manufacturing techniques.

A yet further object of the present invention is to provide a method for producing an adhesive bandage and a wrapper or envelope therefor on a continuous basis from a continuous length of a composite bandage and wrapper material. These and other objects of the present invention will be apparent from the ensuing description and claims of the invention.

SUMMARY

Adhesive bandages comprising an elongated strip of material having a centrally located pad area and adjacent adhesive wing portions extending from each side of the pad area are prepared with an integral wrapper from a continuous length of bulky nonwoven fabric material. The width of the material is divided into two major portions designated as the bandage portion and the wrapper portion. The adhesive bandage is formed from the bandage portion by overlapping the center portion of the material in a Z-fold to provide a pad area comprising a triple thickness of the bulky material. The single thickness wing portions of the material extending from each end of the folded pad are permanently compacted to provide a surface suitable for coating with adhesive. The folded edges of the pad are permanently secured to the wing portions of the bandage to prevent unfolding.

The wrapper portion of the bulky nonwoven fabric material is compacted to provide a dense sheet-like structure and simultaneously laminated on one side with a polyethylene film or subsequently coated to provide an adhesive release surface.

The bandage portion of the material with folded Z-pad is compacted at spaced intervals in narrow bands extending transversely to the machine direction of the material to define individual strip bandage units. The material is optionally perforated or otherwise weakened along a line in the machine direction defining the border between the bandage portion and the wrapper portion of the material to facilitate later separation of the bandage from the wrapper.

A pressure-sensitive adhesive is thereupon applied to the wing portions of the bandage and the material folded twice to enclose the bandage portion of the material within the folds of the wrapper portion with the polyethylene film or other release surface of the wrapper facing the adhesive coated surface of the bandage.

The folded material is die cut with edge sealing along lines transverse to the machine direction of the material and in registry with the narrow bands defining the individual bandage units within the interior of the wrapper to obtain individual wrapped bandages.

When needed for use, access to the bandage is gained by unfolding the wrapper and separating the bandage from the wrapper along the border between the bandage portion and the wrapper portion.

The bandage material is preferably a heat-bondable, absorbent, nonwoven fabric which provides loft and absorbency in the pad area, while the single thickness wing portions of the bandage and the wrapper portion are heat calendered to provide a dense, sheet-like material.

The nonwoven fabric is preferably composed of absorbent fibers such as cellulose or rayon and heat-fusible fibers such as polyethylene or polypropylene in such relative proportions that the pad of the finished bandage is soft and absorbent while the heat-bonded and compacted areas are strong and stable.

DESCRIPTION OF DRAWINGS

FIG. 1 is an end view in perspective of the nonwoven fabric and film used to produce an adhesive bandage and wrapper of the present invention.

FIG. 2 is an end view in perspective illustrating the division of the nonwoven fabric into wrapper and bandage portions in the machine direction.

FIG. 3 is an end view in perspective illustrating the formation of the Z-fold pad of the bandage of the present invention.

FIG. 4 is an end view in perspective of the fabric after definition of the individual bandage units and application of adhesive.

FIG. 5 is an end view in perspective illustrating the initial fold of the bandage portion to the wrapper portion.

FIG. 6 is an end view in perspective illustrating the final fold of the bandage portion and wrapper portion.

FIG. 7 is an edge view in cross section through line 7—7 of FIG. 6 illustrating the configuration of a single wrapped bandage.

FIG. 8 is an end view in cross section through line 8—8 of FIG. 7 illustrating the configuration of the pad area in a wrapped bandage and the final separation and sealing of individual bandage units from the continuous feed of material.

FIG. 9 is an end view in perspective illustrating an alternative embodiment in the material used to produce a bandage and wrapper according to the present invention.

FIG. 10 is an edge view in cross section illustrating the configuration of the wrapped bandage produced from the material of FIG. 9.

FIG. 11 is an end view in perspective illustrating a further embodiment in the material used to produce a bandage and wrapper according to the present invention.

FIG. 12 is an edge view in cross section illustrating the configuration of the wrapped bandage produced from the material of FIG. 11.

DETAILED DESCRIPTION OF THE INVENTION

Strip adhesive bandages of the present invention having a unitized bandage and intregal wrapper are fabricated from a continuous length of bulky nonwoven bandage material.

A preferred bandage material is a bulky, heat-fusible, absorbent, nonwoven fabric comprising a mixture of cellulose or other absorbent fibers and polyethylene or other heat-fusible fibers. The heat-fusible fibers are interspersed throughout the fabric and are preferably present in an amount of at least 10% by weight. The fabric preferably has sufficient thickness or bulk so that the triple-layered pad has a thickness of at least 2 mm in the final bandage. Nonwoven fabrics useful in the practice of the present invention are known in the art for use in other applications. See, for example, U.S. Pat. Nos. 2,774,128; 3,067,747; 4,083,913; 4,160,159; and 4,307,721.

A preferred bandage material is a low density, highly absorbent, thermal bonded nonwoven fabric comprising absorbent fibers and staple length polyester-polyethylene conjugate fibers. These nonwoven fabrics are produced by a process which includes producing a web comprising absorbent fibers and staple length polyester/polyethylene conjugate fibers; subjecting the web to a temperature sufficient to fuse the lower melting component of the conjugate fibers without fusing the higher melting component while maintaining the web under little or no compression; and cooling the web to resolidify the lower melting component of the conjugate fibers, thereby forming a nonwoven fabric bonded at sites where the conjugate fibers touch each other and adjacent absorbent fibers.

A particularly preferred nonwoven fabric is a laminate comprising a core of a mixture of short-length natural cellulose fibers and staple length polyester/polyethylene conjugate fibers, and a light weight veneer of heat-fusible fibers on each surface of the core. The composite web is passed through a through-air heater to fuse the lower melting component of the conjugate fibers while maintaining the fibrous integrity of these fibers, and to fuse or soften the surfaces of the heat-fusible fibers in the two outer veneers. As the material emerges from the heater and cools, the fused surfaces of the lower melting component of the conjugate fibers, i.e., the polyethylene, solidify, and bonds form where these surfaces touch each other and other fibers.

The thermal-bonded, nonwoven fabrics particularly useful in the practice of the present invention employ polyester/polyethylene conjugate fibers wherein at least about 50 percent of the surface of the individual fibers is polyethylene. Most preferred are sheath/core fibers with the polyethylene as the sheath and the polyester as the core. The fibers will usually have a denier within the range of from about 1 to about 6, and a length within the range of from about ½ inch to about 3 or 4 inches.

Absorbent fibers employed in such thermal-bonded, nonwoven fabrics include rayon staple fibers, cotton fibers, short length natural cellulose fibers such as wood pulp fibers and cotton linters, and mixtures thereof.

Heat-fusible fibers used in the veneer of the nonwoven fabric are preferably staple length conjugate fibers. However, if desired, other types of heat-fusible fibers such as polypropylene homofil fibers can be used in the veneer. The veneer can also contain other fibers, such as rayon, cotton, or polyester staple fibers.

The above bonded, nonwoven fabrics normally have basis weights from about ½ to about 6 ounces per square yard. The bulk density of the fabrics is usually below about 0.15 gram per cubic centimeter, preferably below about 0.09 gram per cubic centimeter, e.g., from about 0.02 to about 0.09 gram per cubic centimeter, and more preferably, from about 0.025 to about 0.06 gram per cubic centimeter. The fabrics preferably have an absorbent capacity, as measured by a Gravimetric Absorbency Tester, of at least 600 percent and preferably at least 1400 percent, exclusive of any nonabsorbent layer such as a veneer of 100 percent fusible fibers.

The process of preparing adhesive strip bandages with an integral wrapper from a continuous source of a nonwoven fabric in a preferred embodiment of the present invention will be better understood by reference to FIGS. 1 through 8. In FIG. 1 there is illustrated nonwoven fabric 10 divided into two major portions A and B by broken line 11 extending lengthwise in the machine direction of the material. Portion A is designated to form the wrapper while portion B is designated to form the bandage to be enclosed by the wrapper. Line 11 is a perforated or otherwise weakened line which allows the bandages to be readily separated from the wrapper at the time of use. Also illustrated in FIG. 1 is polyethylene film 20 which ultimately will form an adhesive release surface for the folded wrapper.

In FIG. 2, the various individual areas of material 10 comprising specific portions of the final bandage and wrapper product are indicated as (a) through (h). These areas will be referenced in the following figures whereupon their relative functions will become apparent.

FIG. 3 illustrates in detail the formation of the folded Z-pad of the bandage portion of the product which comprises areas (e), (f) and (g) with areas (d) and (h) extending from the pad area to ultimately form the adhesive wings of the bandage.

FIG. 4 illustrates the full width of fabric 10 with Z-fold 12 extending down the center of bandage portion B, the edges of the Z-fold having been heat fused to the adjacent wing portions to prevent unfolding. Wing areas (d) and (h) together with the entire area of wrapper portion A have been calendered and heat-fused into a dense, sheet-like material. Polyethylene film 20 has been fused to the underside of wrapper portion A during the calendering operation. Individual bandage units have also been defined by compacting portion B along bands 13 extending transversely to the machine direction of the fabric and spaced at regular intervals corresponding to the desired width of the finished bandage product. As further illustrated in FIG. 4, pressure-sensitive adhesive 30 has been applied to wing areas (d) and (h) of the bandage.

The folding of the bandage and integral wrapper of FIG. 4 to form the final product is illustrated in FIGS. 5 and 6 wherein the bandage portion is first folded along line 16 to underlie area (c) of the wrapper portion (FIG. 5) then folded a second time along line 17 (FIG. 6) to underlie area (b) of the wrapper and sealed along line 14 to secure the fold. Area (a) forms flap 15 which remains free for grasping as a means of opening the package. Areas (b) and (c) form the outer surfaces of the wrapper as illustrated in FIG. 6.

The configuration of the folded bandage and wrapper are illustrated in enlarged detail in FIG. 7 which is a section taken lengthwise through the bandage of FIG. 6 along line 7—7.

FIG. 8 is a further enlarged view in section taken crosswise through the folded bandage of FIG. 7 along line 8—8. Individual bandages are sheared from the continuous strip of material and edge sealed by cutting, for example, with a hot knife to fuse the outer edges of the wrapper material. As illustrated in FIG. 8, opposing blades 21 and 22 shear the end bandage from the next adjacent bandage 23 illustrated in phantom. To prevent the bandage pad from interferring with the shearing action or the edge sealing of the wrapper, the line of shear is centered over bands 13 which have been previously impressed on the pad as described above. The width of bands 13 as illustrated in FIG. 8 is exaggerated for clarity.

Other bandage configurations and constructions utilizing the inventive concepts of the present invention will be apparent to those skilled in the art, the principal feature of the present invention being the total construction of an adhesive bandage and integral wrapper utilizing a single continuous length of bandage and wrapper material, preferably a nonwoven fabric comprising heat-fusible fibers.

One alternative bandage construction is illustrated in FIG. 9 wherein areas (a) and (b) of the wrapper which, in the previous embodiment, comprised a laminated nonwoven fabric and polyethylene film, now comprise a heavier guage self-supporting polyethylene film 25, while area (c) of the wrapper portion is composed of an extension of the nonwoven fabric of bandage portion B. The film of area (b) overlaps the fabric of area (c) at 26 and is secured thereto by heat-sealing or other suitable means. The bandage is completed by folding the bandage portion along line 18 to underlie wrapper area (c) with the adhesive surface to the outside, and the thereafter folding the wrapper portion along line 19 so that area (b) overlies the adhesive surface of the bandage as illustrated in FIG. 10. The wrapper is finally closed by heat-sealing along line 14 leaving flap 15 projecting from the end of the package.

FIG. 11 illustrates a further alternative embodiment of the bandage construction wherein only area (c) of the wrapper portion of the material is laminated with an adhesive release surface in the form of polyethylene film 20. In this embodiment, the bandage portion is first folded along line 27 to overlie area (c) of the wrapper portion with the adhesive-coated surface 30 facing film 20. Area (b) of the wrapper is thereupon folded along line 28 to overlie the bandage material and heat-sealed along line 14 as illustrated in FIG. 12.

The bandage configuration of FIG. 7 is generally preferred because the adhesive surface of the bandage is exposed as soon as the wrapper is opened and the bandage is readily applied and separated from the wrapper. In addition the polyethylene film completely envelopes the bandage to assure an enclosure which is waterproof and resistant to the entry of bacteria. The only discontinuity of the polyethylene film in this embodiment is along the seal lines which are nevertheless densely compacted and resistant to the entry of contamination.

In a further alternative embodiment, the wrapper portion of the fabric material may be coated or impregnated with a polymeric composition such as polyethylene, polypropylene or a silicone polymer to impart adhesive release properties to the material while simultaneously assuring a contamination resistant package. In such an embodiment, the polyethylene film laminated to the fabric as previously described may be omitted.

The bandage material can be further modified by incorporating fiber finishes to vary absorbency characteristics or by incorporating medicaments such as bactericides and antibiotics. The surface of the pad intended for placement against the wound may be heat glazed or otherwise surface modified to provide wound release characteristics. These and other variations of the present invention will be readily apparent to those skilled in the art and are included within the scope hereof.

I claim:

1. A method for the continuous production of a plurality of adhesive bandage strips enclosed in an integral wrapper from a continuous length of a bulky, nonwoven fabric comprising the steps of
   (a) forming a continuous length of a bulky, nonwoven fabric comprising a bandage portion and adjacent wrapper portion,
   (b) lapping the central area of said bandage portion in a Z-fold to form a triple thickness pad area extending down the length of said bandage portion with single thickness wing areas extending outward therefrom,
   (c) securing the folded central pad area of the bandage portion to prevent the unfolding thereof,
   (d) compacting said wrapper portion and said single thickness wing areas of said bandage portion to a dense, sheet-like structure,
   (e) applying an adhesive coating to one surface of said compacted wing areas of said bandage portion,
   (f) folding said wrapper portion around said bandage portion to cover both surfaces thereof, said wrapper portion having adhesive release properties over at least that area of the surface thereof in contact with adhesive-coated surfaces of said bandage portion,
   (g) sealing the edge of said wrapper portion to the underlying edge of said bandage portion to enclose the bandage portion within the wrapper, and
   (h) cutting said folded wrapper and enclosed bandage portion into narrow strips transversely to the machine direction thereof and sealing the cut edges of said wrapper to the underlying bandage whereby to obtain an adhesive strip bandage fully enclosed within said wrapper.

2. A method of claim 1 wherein said bulky nonwoven fabric comprises heat-fusible fibers.

3. A method of claim 2 wherein said wrapper portion is compacted into said dense, sheet-like structure by hot calendering.

4. A method of claim 3 wherein at least a portion of said compacted wrapper is coated or impregnated with a polymeric composition which imparts adhesive release properties to the material.

5. A method of claim 4 wherein said polymeric composition is polyethylene, polypropylene or a silicone polymer.

6. A method of claim 3 wherein at least a portion of said wrapper is laminated to a polymeric film having adhesive release properties.

7. A method of claim 6 wherein said polymeric film is polyethylene or polypropylene.

8. A method of claim 1 wherein said wrapper includes a polymeric film affixed to and extending from said compacted wrapper portion of said nonwoven fabric, said polymeric film being in contact with the adhesive surface of the bandage enclosed by said wrapper.

9. A method of claim 8 wherein said polymeric film is polyethylene or polypropylene.

10. A method of claim 2 wherein said nonwoven fabric comprises a mixture of absorbent fibers with at least 10% heat-fusible fibers.

11. A method of claim 11 wherein said heat-fusible fibers are staple length polyester core/polyethylene sheath conjugate fibers.

12. A method of claim 2 wherein said nonwoven fabric comprises a core of a mixture of absorbent fibers and heat-fusible polyester/polyethylene conjugate fibers and an outer veneer of heat-fusible polyester or polyethylene fibers on both faces of said core.

13. A method of claim 12 wherein said absorbent fibers are selected from the group consisting of rayon, cotton, wood pulp, cotton linters, and mixtures thereof.

14. A method of claim 12 wherein the wound facing surface of the pad of said bandage is heat-glazed to impart nonsticking wound release properties thereto.

* * * * *

UNITED STATES PATENT AND TRADEMARK OFFICE
CERTIFICATE OF CORRECTION

PATENT NO. : 4,607,633

DATED : August 26, 1986

INVENTOR(S) : Nels J. Lauritzen

It is certified that error appears in the above-identified patent and that said Letters Patent is hereby corrected as shown below:

column 8, line 4

"11. A method of claim 11"

should read --11. A method of claim 10--

Signed and Sealed this

Twenty-seventh Day of January, 1987

Attest:

DONALD J. QUIGG

*Attesting Officer*     *Commissioner of Patents and Trademarks*